United States Patent [19]
Wohlgemuth

[11] Patent Number: 5,496,173
[45] Date of Patent: Mar. 5, 1996

[54] DENTAL HANDPIECE HAVING AN AUTOMATICALLY CONTROLLED TURBINE DRIVE

[75] Inventor: Juergen Wohlgemuth, Darmstadt, Germany

[73] Assignee: Siemens Aktiengesellschaft, Munich, Germany

[21] Appl. No.: 261,149

[22] Filed: Jun. 14, 1994

[30] Foreign Application Priority Data

Jun. 21, 1993 [DE] Germany .......... 43 20 532.1

[51] Int. Cl.⁶ .................................. A61C 1/05
[52] U.S. Cl. .................................. 433/132; 415/904
[58] Field of Search .................... 433/114, 115, 433/132; 415/146, 148, 904

[56] References Cited

U.S. PATENT DOCUMENTS

| | | | |
|---|---|---|---|
| 3,088,707 | 5/1963 | Williams et al. | 433/132 X |
| 3,132,426 | 5/1964 | White | 433/132 |
| 3,386,702 | 6/1968 | Krzyszczuk . | |
| 3,578,872 | 5/1971 | McBurnie | 415/25 |
| 3,708,240 | 1/1973 | Theis, Jr. et al. | 433/132 X |
| 3,733,143 | 5/1973 | Theis, Jr. | 433/132 X |
| 3,767,320 | 10/1973 | Theis, Jr. et al. | 433/132 X |
| 3,865,505 | 2/1975 | Flatland . | |
| 4,060,336 | 11/1977 | Theis, Jr. et al. | 415/904 X |
| 4,341,520 | 7/1982 | Wallace | 433/132 |
| 4,723,911 | 2/1988 | Kurtz . | |
| 4,744,752 | 5/1988 | Nakayama et al. . | |
| 5,364,227 | 11/1994 | Franetzki et al. . | |

FOREIGN PATENT DOCUMENTS

| | | |
|---|---|---|
| 0283417 | 9/1988 | European Pat. Off. . |
| 0497139 | 8/1992 | European Pat. Off. . |
| 0549910 | 7/1993 | European Pat. Off. . |
| 845092 | 7/1952 | Germany . |
| 1238311 | 10/1967 | Germany . |
| 1277516 | 5/1969 | Germany . |

*Primary Examiner*—Nicholas D. Lucchesi
*Attorney, Agent, or Firm*—Hill, Steadman & Simpson

[57] ABSTRACT

A controllable turbine drive for a dental handpiece has an adjustment member which rotates with the rotor disc and is deformable due to the centrifugal forces to constrict an exhaust channel extending along the disc to change the effective cross section of the channel so that with an increased speed of rotation, the effective cross section decreases and with a decreased speed, the effective cross section is increased. The member may be an elastic ring which is restrained by a rim formed by a recess on one side of the rotor disc or it may be an elastic spring washer, which has an upturned peripheral flange and which is bent or elastically deformed.

11 Claims, 2 Drawing Sheets

DENTAL HANDPIECE HAVING AN AUTOMATICALLY CONTROLLED TURBINE DRIVE

BACKGROUND OF THE INVENTION

The present invention is directed to a dental turbine drive which contains a rotor disc guided in bearings. The rotor disk comprises a plurality of turbine buckets on the periphery of the rotor that can be charged with compressed air via a nozzle disposed in the housing of the handpiece and the turbine drive includes adjustment means for controlling the turbine speed being disposed in the flow path of the exhaust air from the turbine.

Turbine drives have been utilized for a long time in dental turbine handpieces and are distinguished over other drives by a relatively simple structure as well as a comparatively simple arrangement for supplying power to the drive. However, they are affected by the disadvantage of a relatively low eroding power and what is usually an excessively high no-load speed, which may extend up to a maximum of 400,000 rpm. When a load is applied to the tool being driven, the speed of the turbine will abruptly drop. The high speed will also cause a relatively high wear of the bearings, which may be either plain bearings or ball bearings. Moreover, there is a risk that the eroded material, for example a dental substance, will heat to an inadmissible extent or will even be burned given the relatively high speed of the turbine as the tool, such as a drill, first contacts the material to be eroded, such as a tooth.

German Patent 845 092 discloses a dental turbine drive and the speed of the turbine can be varied by varying the cross section of outlet openings for the compressed air flowing off from the turbine. The discharge channel is formed between two cylindrical parts, which are arranged concentrically relative to one another, and each of these parts has a plurality of openings on a circumference. Thus, a variation of the cross section of the outlet openings can be obtained by displacing the outer cylindrical part or sleeve on the inner part so as to change the amount of coincidence of the openings of the two parts by either increasing the coincidence or decreasing the coincidence. The displacement of the outer cylindrical part occurs manually with a lever that extends along the outside of the handpiece.

The arrangement of this publication discloses a possibility of setting a speed desired by the user of the handpiece but does not disclose any measures for an automatic regulation of the speed depending on the load being applied to the tool rotated by the turbine drive.

U.S. Pat. No. 3,865,505, whose disclosure is incorporated herein by reference thereto, discloses control means for a dental turbine wherein a valve that is controlled dependent on the volume throughput of the returned air is arranged in the delivery channel for the compressed air being introduced to the turbine drive. When the speed of the turbine drops due to an external load, then the valve in the delivery channel is opened and a greater volume of air is conducted to the rotor disc of the turbine drive. The control of the inlet air stream dependent on the returned air can occur in various ways in the turbine of this patent. For example, among other things, a spring-loaded slide in the return air channel will control a valve in the inlet air channel or a membrane or diaphragm is arranged in the return air channel which will displace a piston that will control the flow in the inlet channel. The speed can be kept constant independently of load with this known control means. The apparatus has, among other things, the disadvantage that relatively great forces are necessary for throttling the overall air stream, and these forces can be produced in the exhaust air channel only given employment of volume and mass. However, an unstable control behavior of the turbine is, thus, created. In addition, the known device requires a relatively large structure within the turbine handpiece and, therefore, integration problems can arise as a result of this necessary size.

U.S. Pat. No. 3,578,872, whose disclosure is incorporated herein by reference thereto, discloses a two-stage turbine drive provided for a drive of a surgical tool. The drive is provided with measures, on the one hand, to limit the maximum speed of the turbine in order to thereby avoid what is referred to as overspeeding of the turbine and, in addition, in order to increase the torque under load. The measures provided for this purpose are composed of an annular part rotating together with the turbine wheel that has a circumferential rim on the periphery and an annular space for receiving an elastic ring is formed between this peripheral rim and part of the rotor or armature sleeve of the part. The elastic ring will expand with increasing speed as a consequence of the centrifugal force and thereby will close openings provided on an end face of the part so that the throughput volume of the air will be reduced. The effective cross section can be varied by these measures and the maximum speed of the turbine can be ultimately limited.

The setting or, respectively, variation of speed here occurs in a known way by varying the volume of the supplied air on the basis of an additional manually-actuatable control valve that is not shown in that patent.

SUMMARY OF THE INVENTION

The object of the present invention is to provide a dental turbine drive that, in view of the measures for an automatic speed control dependent on load changes and is constructed more simply requires less space and assures a high reliability in comparison to the prior art devices.

To accomplish these goals, the present invention is directed to an improvement in a dental handpiece having a turbine drive including a rotor disc having a plurality of blades on a circumference thereof, said rotor disc being mounted by bearings for rotation in a chamber of a housing of the handpiece with the blades being positioned to be charged with a compressed air from a nozzle located in the housing and adjustment means being disposed in the flow path of the exhaust air for regulating the turbine speed. The improvements comprise the outlet channel being formed between the rotor disc and an annular wall of the chamber in the housing, said adjustment means being a member mounted to rotate with the rotor drive and said member being resiliently deformed by centrifugal force to deform into the outlet channel so that with increasing speeds, the member deforms into the channel to decrease the effective cross sectional area of the channel and with the reduced speeds the effective cross section area increases to increase the flow rate to allow an increase in speed of the rotor.

Other advantages and features of the invention will be readily apparent from the following description of the preferred embodiments, the drawings and claims.

DESCRIPTION OF THE PREFERRED EMBODIMENTS

Figure 1:
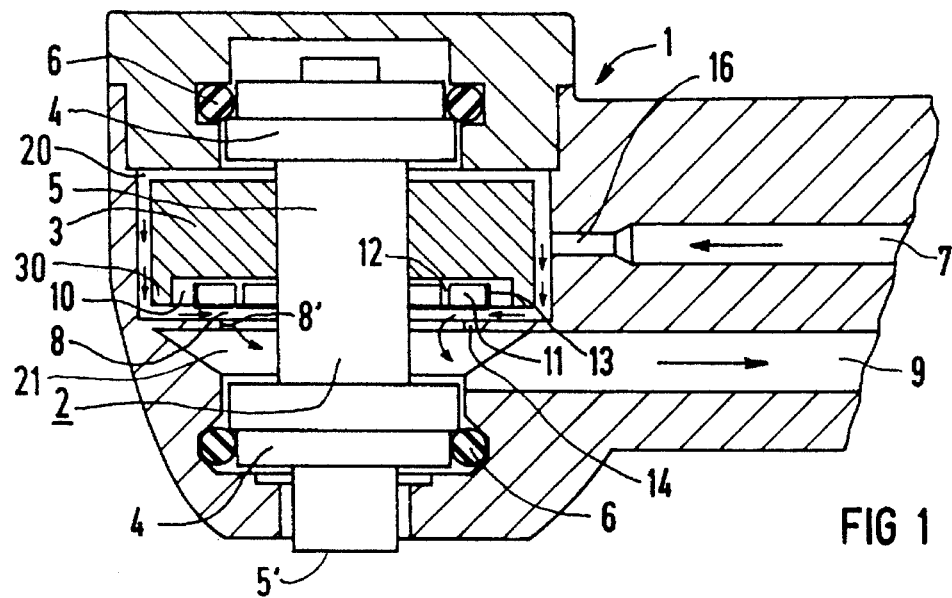
FIG. 1 is a cross sectional view of the first embodiment of the handpiece with the inventive turbine drive operating in a low-speed condition.

The principles of the present invention are particularly useful when incorporated in a dental handpiece having a turbine drive, generally indicated at 2, disposed in a head housing 1 of the handpiece. The turbine drive or drive unit 2 contains a rotor disc 3 which is mounted on a shaft 5 that is mounted in a chamber 20 in the head housing 1 by a pair of bearings 4. A lower or exposed end 5' of the shaft will have a chuck or socket for receiving the tool, such as a dental drill. The rotor disc 3 has a plurality of buckets on an outer periphery, which are presented to receive compressed air from a nozzle 16 that is in the wall of the chamber 20. The nozzle 16 receives a supply of compressed air from a delivery channel 7, which will flow in the direction of the arrows. To prevent vibration and to dampen vibration, O-rings, such as 6, are provided adjacent each of the bearing units 4. This arrangement is a known arrangement similar to that disclosed in German Patent Nos. 12 77 516 and 12 38 311.

As mentioned above, the compressed air is supplied by channels 7 through the nozzle 16, is directed on the buckets of the rotor 3 and is then exhausted to a return air channel 9 via an outlet channel 8 after flowing through the turbine buckets of the rotor disc. By contrast to previously-known designs, the outlet channel 8 discharges into an exhaust air channel or chamber 21 which is located outside the turbine space limited by the rotor disc 3 and a rotor disc housing. An advantage of this chamber structure is that the re-circulating effect, which occurs, as known, given a coasting turbine, is avoided.

Figure 3:
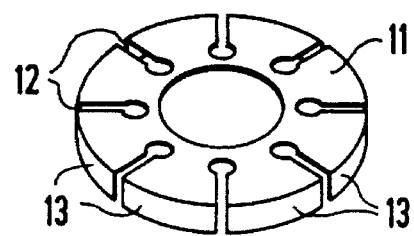
FIG. 3 is a perspective view of the disc used in the adjustment means.

Facing toward the outlet channel 8, the rotor disc 3 contains a recess 10, which proceeds concentrically relative to the shaft and forms a rim 30. Adjustment means in the form of a resilient disc or spring washer 11 having an upturned annular flange or rim 13 is arranged by the recess 10 for automatic speed regulation. The disc 11 is shown in perspective in FIG. 3 and comprises a plurality of slots 12 which are directed radially-like and lend the disc a particular elasticity. As may be seen from FIG. 1, the disc 11 is placed on the shaft 6 with the rim or edge 13 extending inwardly into the recess 10. Together with the annular housing wall 14, which defines an axial opening 8', the disc 11 will limit the effective cross section over which the compressed air can flow off through the channel 8.

Figure 2:
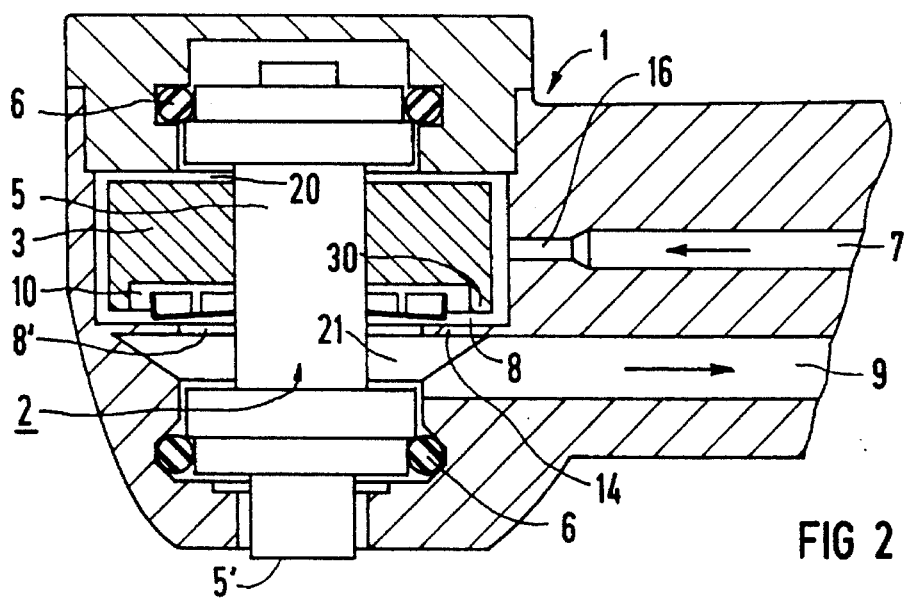
FIG. 2 is a cross sectional view similar to FIG. 1 showing the first embodiment with the adjustment arrangement restricting flow.

During operation, for example when the rotor disc rotates, the centrifugal force acts on the disc 11, namely such that the free ends of the disc bend away from the rotor disc 3, as illustrated in FIG. 2. As a result thereof, the cross sectional gap between the disc 11 and rotor disc housing wall 14 is constricted. Since the outflowing air stream passes through this gap, the air stream can be throttled on the basis of a suitable dimensioning of the gap and disc 11. A reduced no-load speed can be set as desired. The speed drops when a load is applied during preparation. An excessive decrease, however, is prevented since the excursion of the disc lessens when the speed drops and, as a result, the gap and, thus, the air stream passing therethrough become greater.

Figure 4:
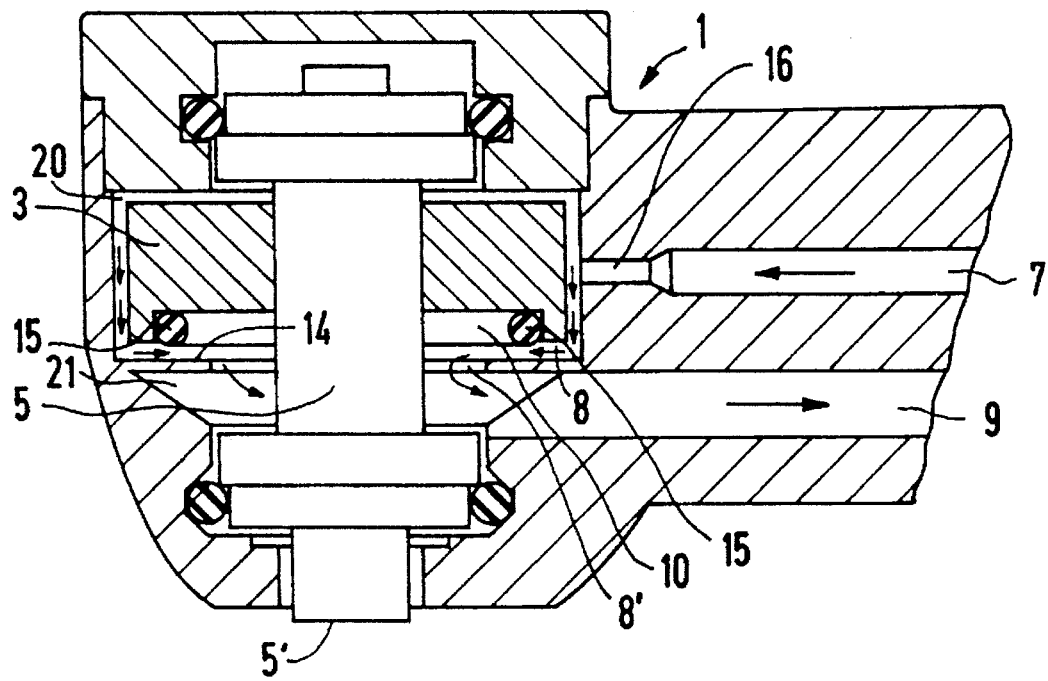
FIG. 4 is a cross sectional view of a second embodiment of an adjustment means of the turbine drive of the present invention in a retracted or low-speed condition.
Figure 5:
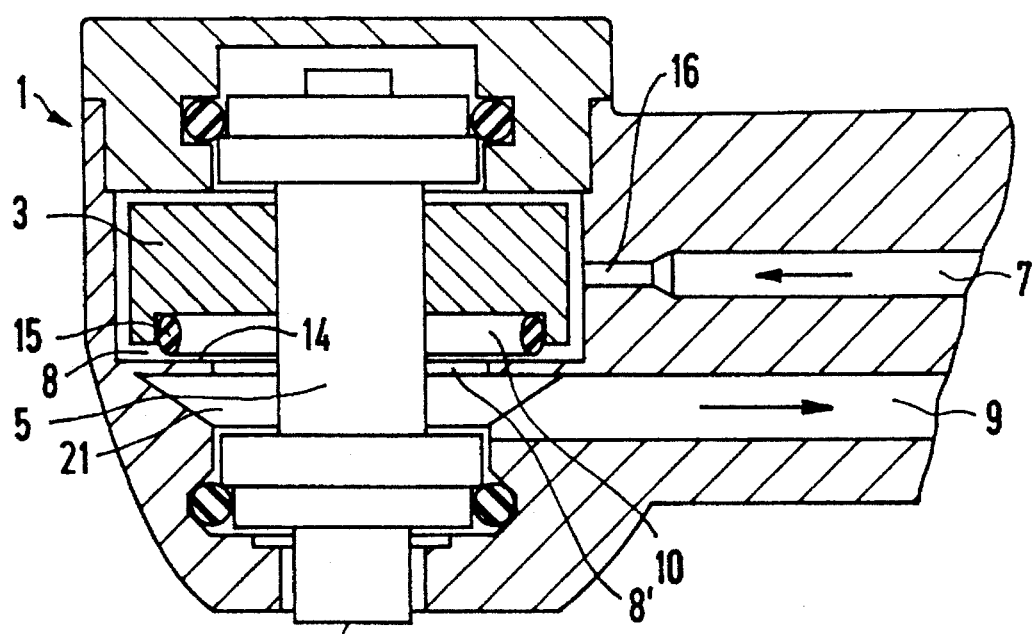
FIG. 5 is a cross sectional view similar to FIG. 4 with the control means restricting the flow to slow the turbine drive.

In the embodiment illustrated in FIGS. 4 and 5, the adjustment element is an elastic O-ring 15, whose elasticity is selected so that its shape and/or position in a recess 10 of the rotor 8 will change due to the influence of centrifugal force. Thus, the cross section in the output channel 8 is reduced at high speeds but is enlarged given a diminished speed. For this purpose, the O-ring is placed in the recess 10 so that it presses against the outside wall or rim 30 of the recess. The cross section which is circular in the idle condition illustrated in FIG. 4, will then resiliently deform to form an oval cross section illustrated in FIG. 5. As a result of this deformation, as already mentioned, the gap between the rotor disc 3 and the housing wall 14 decreases to constrict the flow through the channel 8.

The adjustment means is advantageously arranged at only one face side of the rotor. It is conceivable and is within the scope of the invention to also arrange a corresponding adjustment means at the opposite face side.

Although various minor modifications may be suggested by those versed in the art, it should be understood that I wish to embody within the scope of the patent granted hereon all such modifications as reasonably and properly come within the scope of my contribution to the art.

I claim:

1. In a dental handpiece having a turbine drive including a rotor disc having a plurality of blades on a circumference thereof, said rotor disc being mounted for rotation on an axis in a turbine chamber of a housing of the handpiece with the blades being positioned to be charged with a tangential inflow of compressed air from a nozzle located in the housing, and adjustment means being disposed in the flow path of the exhaust air for regulating the turbine speed, the improvement comprising the rotor disc having an end face with a recess with a cylindrical annular wall, an outlet channel being formed between the rotor disc and a radially extending annular wall of the turbine chamber in the housing, said adjustment means being an elastically deformable ring arranged concentrically on the axis of the rotor disc in said recess to rotate with the rotor disc and said ring being resiliently deformed against the annular wall by centrifugal forces to be deformed from a circular cross section to an oval cross section extending in an axial direction into the outlet channel so that with increasing speeds, the ring deforms into the outlet channel to decrease the effective cross sectional area of the outlet channel and with a reduced speed, the ring withdraws from the outlet channel to increase the effective cross sectional area thereof.

2. In a dental handpiece according to claim 1, wherein, adjacent the recess of the rotor disc, the outlet channel passes through an annular port surrounding an axis of said rotor into a second chamber connected by an exhaust air channel extending into the handle of the handpiece.

3. In a dental handpiece according to claim 1, wherein the outlet channel is formed by a wall of the housing and extends into an axially aligned opening connected to a second chamber outside of the chamber receiving the rotor disc so that the exhaust air channel is arranged outside of the turbine chamber.

4. In a dental handpiece having a turbine drive including a rotor disc having a plurality of blades on a circumference thereof, said rotor disc being mounted for rotation in a chamber of a housing of the handpiece with the blades being positioned to be charged with compressed air from a nozzle located in the housing, and adjustment means being disposed in the flow path of the exhaust air for regulating the turbine speed, the improvement comprising an outlet channel being formed between the rotor disc and an annular wall of the chamber in the housing, the rotor disc having an end face recess, said adjustment means being a spring washer having an annular lip, said washer being mounted to rotate with the rotor disc and with the lip extending into the recess, said washer being resiliently deformed by centrifugal forces to be deformed into the outlet channel so that with increasing speeds, the washer deforms into the channel to decrease the effective cross sectional area of the channel and with a reduced speed, the washer withdraws from the channel to increase the effective cross sectional area thereof.

5. In a dental handpiece according to claim 4, wherein the spring washer has a plurality of slots forming spring elastic segments.

6. In a dental handpiece according to claim 5, wherein the slots extend radially outward from the center of the washer.

7. In a dental handpiece according to claim 6, wherein the outlet channel has an axially disposed opening discharging into an exhaust air channel which is located outside of the chamber receiving the rotor disc.

8. In a dental handpiece having a turbine drive including a rotor disc having a plurality of blades on a circumference thereof, said rotor disc being mounted for rotation on an axis in a turbine chamber of a housing of the handpiece with the blades being positioned to be charged with a tangential inflow of compressed air from a nozzle located in the housing, and adjustment means being disposed in the flow path of the exhaust air for regulating the turbine speed, the improvement comprising an outlet channel being formed between the rotor disc and a radially extending annular wall of the turbine chamber in the housing, the rotor disc having an end face recess, said adjustment means being a member, the member being a spring washer having an annular lip, said washer being mounted with the lip extending into the recess and to rotate with the rotor disc, said member being resiliently deformed by centrifugal forces to be deformed in an axial direction into the outlet channel so that with increasing speeds, the member deforms into the outlet channel to decrease the effective cross sectional area of the outlet channel and with a reduced speed, the member withdraws from the outlet channel to increase the effective cross sectional area thereof.

9. In a dental handpiece according to claim 8, wherein the spring washer has a plurality of slots forming spring elastic segments.

10. In a dental handpiece according to claim 9, wherein the slots extend radially outward from the center of the washer.

11. In a dental handpiece according to claim 8, wherein the outlet channel has an axially disposed opening discharging into an exhaust air channel which is located outside of the turbine chamber.

* * * * *